US005891390A

United States Patent [19]

Joslyn

[11] Patent Number: 5,891,390

[45] Date of Patent: Apr. 6, 1999

[54] METHOD FOR REDUCING THE DANGER OF FIRE OR EXPLOSION FROM STERILANT LEAKAGE

[75] Inventor: Larry J. Joslyn, Macedon, N.Y.

[73] Assignee: Joslyn Sterilizer Corporation, Mentor, Ohio

[21] Appl. No.: 586,430

[22] Filed: Jan. 16, 1996

[51] Int. Cl.[6] .......... A61L 2/20

[52] U.S. Cl. .......... 422/2; 422/28; 422/34

[58] Field of Search .......... 422/2, 28, 34, 422/117, 292, 300

[56] References Cited

U.S. PATENT DOCUMENTS

| | | | |
|---|---|---|---|
| 4,770,851 | 9/1988 | Joslyn | 422/26 |
| 4,812,292 | 3/1989 | Joslyn | 422/31 |
| 4,822,563 | 4/1989 | Joslyn | 422/31 |
| 5,008,079 | 4/1991 | Wutzler et al. | 422/28 |

OTHER PUBLICATIONS

F. E. Halleck, "Industrial Sterilization Processes," vol. 18, Chap. 25, pp. 335–351 of Proceedings of 33d General Meeting of the Society for Industrial Microbiology 1976.

*Primary Examiner*—Ivars Cintins
*Attorney, Agent, or Firm*—Fay, Sharpe, Beall, Fagan, Minnich & McKee

[57] ABSTRACT

A novel apparatus and method for sterilizing microbially contaminated materials, e.g., hospital linens, packaged goods, etc., by contact with a flammable chemical sterilant gas such as ethylene oxide, employs a bulk supply vessel for the sterilant gas and a small unit dosage vessel which receives a unit dosage of sterilant gas from the bulk supply vessel. The unit dosage vessel delivers a charge of sterilant gas to a separately enclosed sterilizing chamber in which the materials to be sterilized are placed. Water flooding means in a supply cabinet in which the bulk supply vessel is positioned, protects against possible deflagration of the sterilizing gas in the event of leakage or rupture of the gas supply means.

11 Claims, 2 Drawing Sheets

METHOD FOR REDUCING THE DANGER OF FIRE OR EXPLOSION FROM STERILANT LEAKAGE

FIELD OF THE INVENTION

This invention relates to an apparatus and process, especially useful in the field of sterilization and dispensing potentially hazardous compressed gases and liquids and, more particularly, to such an apparatus and process for storing and dispensing a flammable or toxic sterilizing gas with improved safety.

BACKGROUND

To sterilize microbially contaminated materials such as packaged goods and hospital materials such as towels, sheets, tubing and the like, it is known to treat the materials with a gaseous chemical sterilant. Especially useful are alkylene oxides, e.g., ethylene oxide and propylene oxide. The contaminated materials are contacted in a sterilization chamber with the chemical sterilant at reduced pressure and moderately elevated temperature for sufficient time to sterilize the material. Useful procedures for sterilizing with gaseous chemical sterilants are disclosed, for example in the present inventor's earlier U.S. Pat. Nos. 4,770,851; 4,812,292; and 4,822,563 the disclosures of which, including cited references, are incorporated herein by reference.

Although the alkylene oxides are excellent sterilants, they are flammable, and, under certain conditions, highly explosive. In addition, they may be toxic.

To reduce the danger of using large containers of flammable gaseous sterilants, a common practice has been to provide the sterilization chamber with a small pressurized container or cartridge filled with a unit dosage, e.g., 200 to 250 g, of the flammable sterilant. After each sterilization run, the empty unit dosage cartridge is replaced for the next run with a full cartridge. An advantage of this procedure is that, in the event of a fire, earthquake or other calamity that might cause rupture of a bulk container of ethylene oxide feeding in the sterilization chamber and consequent fire or explosion, only a small amount of the gaseous chemical is present in or near the sterilization chamber.

Unfortunately, the use of small sterilizing gas cartridges does not eliminate all danger. In fact, the common practice of storing a supply of unit dose cartridges at a hospital or factory creates the danger of multiple explosions should a fire occur in the storage place. The unit dosage cartridges do not have pressure relief devices, as do the bulk shipping containers for ethylene oxide that are approved by the U.S. Department of Transportation (DOT). Each cartridge, in effect, is potentially a small bomb. In addition, the disposable cartridges are costly and their use is more expensive than dispensing from a bulk container such as the conventional shipping cylinders that are specially designed for the rigors of shipping. Furthermore, the cartridges must be disposed of as a hazardous material. Their disposal creates an ecologically undesirable landfill waste.

A need exists, therefore, for an improved apparatus and procedure for feeding unit dosages of a gaseous chemical sterilant economically to a sterilizing apparatus with reduced risk of deflagration of the sterilant or of release of toxic materials to the atmosphere. The present invention provides such an improved apparatus and procedure.

BRIEF SUMMARY OF THE INVENTION

The apparatus of the invention comprises a sterilization chamber for holding material to be sterilized and having conduit means for feeding a sterilizing gas into contact with said material, a bulk supply vessel having a storage capacity for multiple dosages of sterilizing gas, a unit dosage vessel positioned in a gas conduit path between said supply vessel and said chamber, said unit dosage vessel being limited in capacity to the volume of a single sterilizing gas charge for said chamber, gas conduit means connecting said bulk supply vessel with said unit dosage vessel and gas conduit means connecting said unit dosage vessel with said chamber, means for controlling the flow of sterilizing gas from said supply vessel to said unit dosage vessel and means for controlling the flow of sterilizing gas from said unit dosage vessel to said chamber.

In a further embodiment, the apparatus of the invention comprises a supply cabinet separate from the sterilization chamber and having containment means for the bulk supply vessel and means for supplying water to the containment means to flood the bulk supply vessel and reduce the risk of fire or explosion.

The chemical sterilization method of the invention comprises storing a multi-dosage amount of a flammable chemical sterilant fluid under pressure in a bulk storage container in a containment zone provided with means for flooding said zone with water, intermittently feeding a unit dosage of said sterilant fluid from said bulk container to a unit dosage container of smaller volume, and intermittently feeding the contents of said unit dosage container to a chemical sterilization chamber containing material to be sterilized.

DRAWINGS

The invention will be described in more detail by reference to the drawings, of which:

FIG. 1 is a flow diagram illustrating the flow of materials in the method of the invention and illustrating schematically an embodiment of the apparatus of the invention; and FIG. 2 illustrates diagramatically a supply cabinet of the invention with parts broken away, including a water flooding means and water scrubbing means.

DETAILED DESCRIPTION

Figure 1:
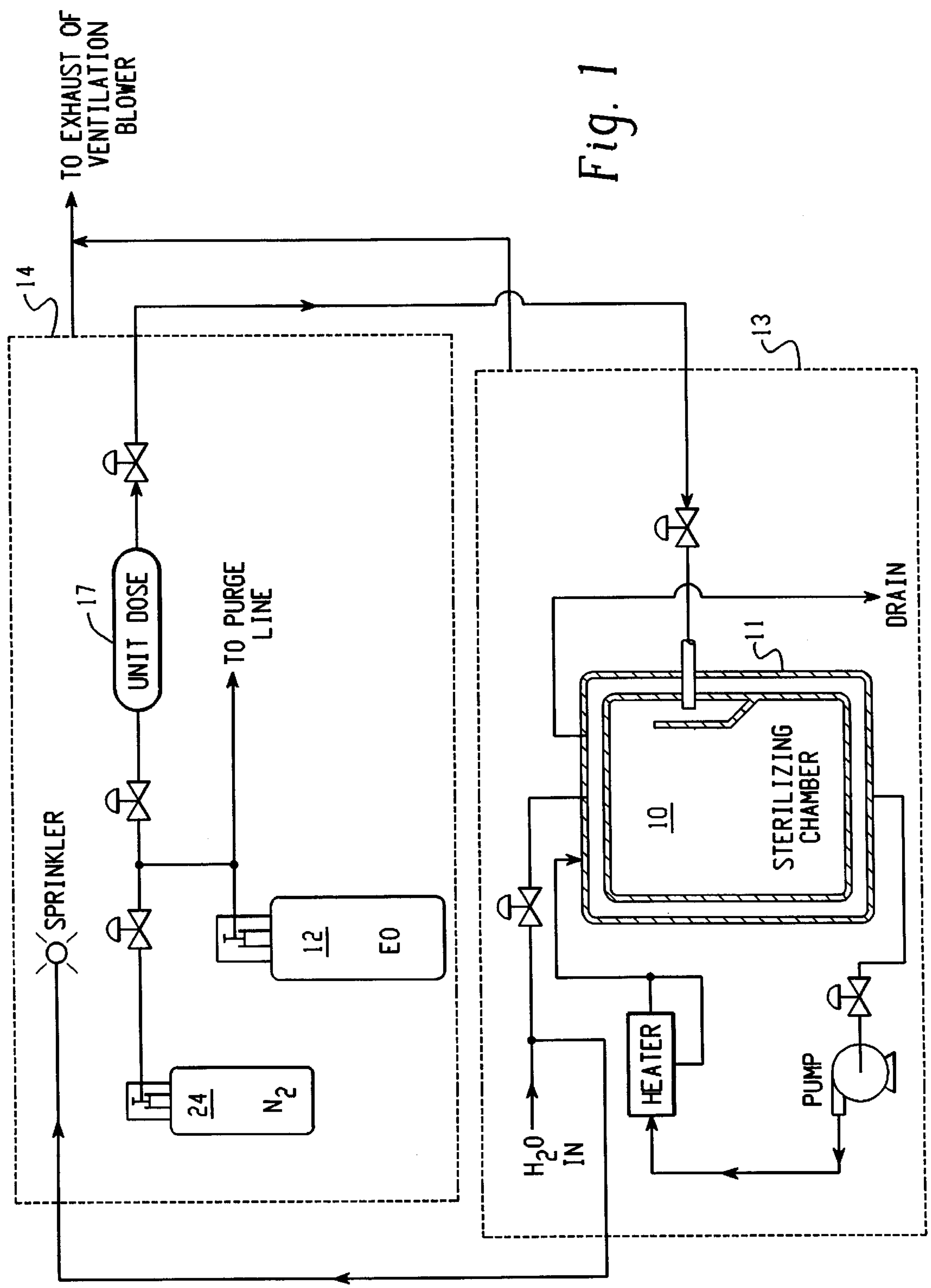

Referring to FIG. 1 a sterilizing chamber 10 in a jacket 11 is enclosed in an outer cabinet 13. The chamber 10 is preferably constructed of stainless steel and is capable of containing a deflagration of flammable sterilant gas. More particularly, the sterilizing chamber 10 designed with walls and joints of sufficient strength to have a pressure rating which contains the deflagration of ethylene oxide sterilant gas within the chamber 10 for the unit dose of such sterilant which is dispensed into the chamber from a unit dosage container 17, which is described in detail hereinafter. Chamber 10 is normally maintained under negative or subatmospheric pressure by a vacuum pump via conduits not shown in the drawing in order to keep any gases from leaving the chamber and entering the surrounding area.

An outer cabinet 13 encloses the sterilizing chamber 10 and its jacket 11. The outer cabinet 13 prevents the formation of a flammable concentration of sterilant gas around the chamber 10 and its jacket 11. The cabinet 13 is made of materials selected so as not to support combustion in the event of a fire. The cabinet 13 is also ventilated with air to prevent the accumulation of the sterilant (ethylene oxide gas) around the sterilizing chamber, jacket and the piping associated therewith.

Ethylene oxide sterilant is supplied to the process from a bulk supply vessel 12 which is preferably a shipping container of the type conforming to governmental requirements for gas shipping containers or cylinders. In the presently preferred embodiment of the invention, the bulk supply vessel 12 is enclosed within a supply cabinet 14 which is separate from the cabinets 11 and 12 and is also capable of preventing the formation of flammable concentrations of sterilant gas.

Figure 2:
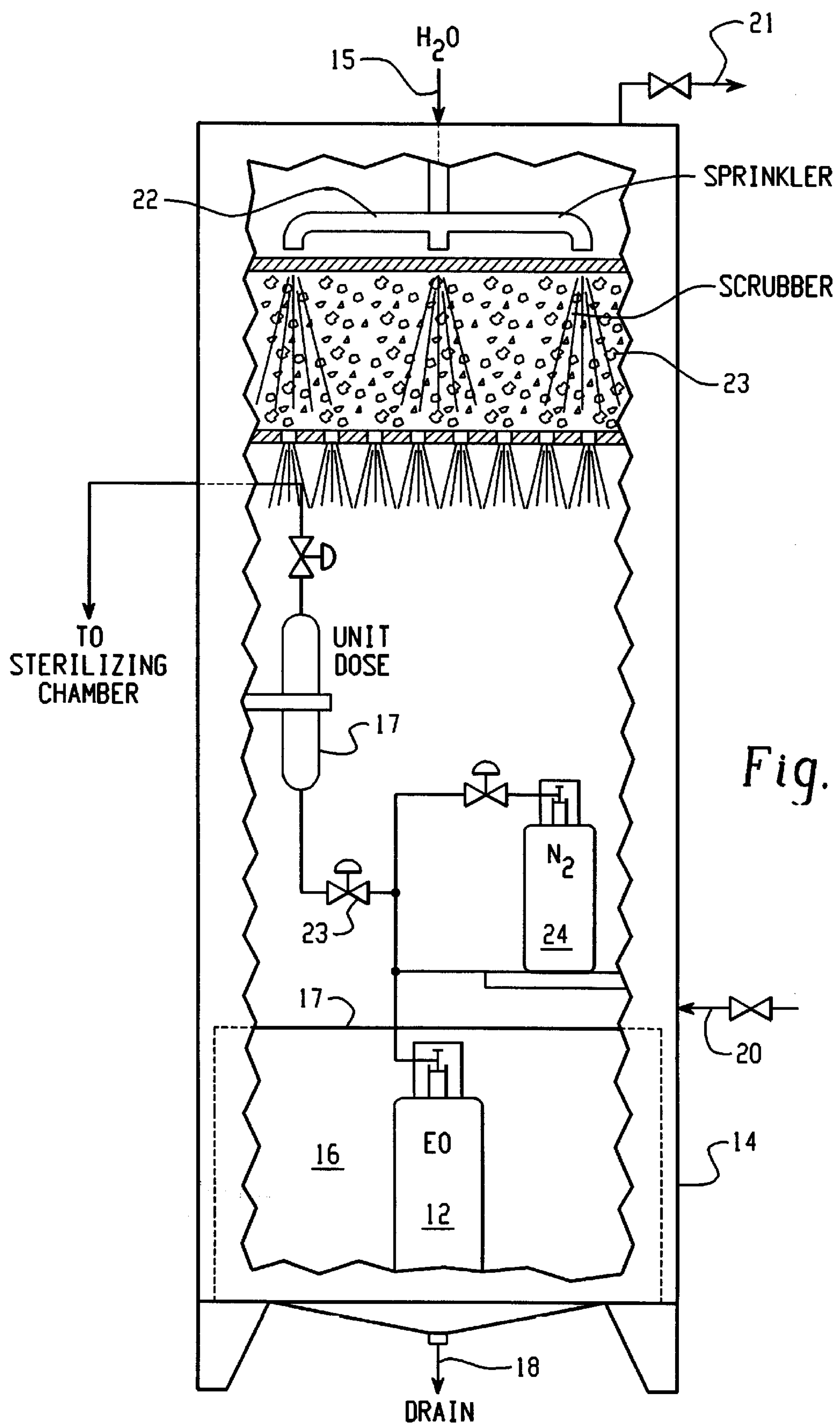

In addition and as shown in FIG. 2, in a lower portion of supply cabinet 14 the bulk supply vessel 12 is positioned in a water-containment zone 16 which is adapted to receive, hold and immerse vessel 12 in a quantity of water in an emergency. Water is supplied to supply cabinet 14 by line 15, the latter having an inlet valve which is opened automatically to flood the bulk supply vessel in the event of loss of air flow for the cabinet ventilation means. The supply cabinet 14 is also provided with a chemical sensor, not shown, which, in accordance with the invention, is used to monitor the atmosphere within cabinet 14 to detect any possible leakage of sterilant gas. If the chemical sensor detects a concentration of ethylene oxide exceeding the lower flammable limit of 30,000 ppm, the containment zone 16 is flooded to immerse vessel 12 in water.

The water-containment zone 16 can be filled with water to the level of its open top or dam 17, thus totally immersing the bulk supply vessel 12 in water. Water overflowing the dam 17 collects at the bottom of cabinet 14 and can be withdrawn by drain 18. In the event of total discharge of ethylene oxide from a supply cylinder 12 of the usual capacity (20 lb.), the ethylene oxide is thereby diluted at least 22:1. At this dilution the solution is non-flammable and can be safely disposed of after withdrawal through drain 18.

In the preferred embodiment shown in FIG. 2, ventilation air is fed to the supply cabinet 14 by line 20 and is withdrawn by line 21 leading to an exhaust ventilation blower, not shown, to maintain a negative pressure in cabinet 14 relative to the surrounding work area and to remove safely any fugitive emissions of ethylene oxide.

In the preferred embodiment of the invention, the supply cabinet 14 also is equipped with an internal water scrubber means including the sprinkler 22 and a packed column zone 23. The latter is filled with permeable packing material such as ceramic particles to provide surfaces for gas-liquid contact. The sprinkler turns on in the event of loss of air flow for the cabinet ventilation or the detection by an integrated chemical sensor, not shown, of ethylene oxide levels above 30,000 ppm which is the lower flammable limit for ethylene oxide. The scrubber absorbs ethylene oxide by countercurrent contact with water in the packed column zone 23 to form a non-flammable solution. This can be suitably disposed of by withdrawal through line 18.

The delivery of a unit dose of ethylene oxide to the sterilizing chamber is accomplished in the method of the invention by filling the unit dosage container 17 with ethylene oxide from the bulk supply container 12. The normal dosage for a sterilizing chamber of 8.8 cubic feet capacity is 200 g. to 250 g. of 100% ethylene oxide. When the sterilizing chamber 10 is ready to receive a charge of sterilant, the outlet line of the unit dose container is opened and ethylene oxide gas is fed to the sterilizing chamber for contact with fabrics, packaged goods or other microbially contaminated material. After its contents are emptied into the sterilizing chamber, the unit dose container 17 can be refilled by opening valve 23 until the correct amount of ethylene oxide is introduced. As shown in FIGS. 1 and 2, within the supply cabinet 14 can also be positioned a cylinder 24 of an inert gas such as nitrogen. The latter can be used to fill the emptied bulk supply vessel 12, and thus avoid the formation of explosive air-sterilant mixtures, when the vessel 12 is to be removed for refilling with ethylene oxide.

As stated above, the sterilizing chamber 10 of FIG. I is enclosed in a vented sterilizer cabinet 11. The sterilizing chamber 10 and cabinet 11 are preferably is of sufficiently rugged construction to withstand or render harmless any possible deflagration of sterilant gas within the chamber. Like the supply cabinet 14, the sterilizing cabinet 11 is maintained under negative pressure to prevent leakage of chamber gases into the surrounding environment and to prevent the formation of a flammable mixture in the surrounding work area. The cabinet ventilation air from the vented sterilizing cabinet 11 and the vented supply cabinet 14 can be removed via a common exhaust duct connecting with a ventilation exhaust blower, not shown.

The following example illustrates an embodiment of the invention.

EXAMPLE

A load of approximately 50 pounds of soiled hospital linen is placed in a sterilizing chamber, such as chamber 10 of FIG. 1, having a capacity of 8.8 ft$^3$. Heated water is circulated through a jacket surrounding the chamber to maintain its temperature at about 135° F. A charge of 200 g. of 100% liquified ethylene oxide under a pressure of about 50 PSIG is fed from a bulk supply cylinder such as cylinder 12 of FIGS. I and 2 to a unit dosage vessel, such as vessel 17 of FIGS. 1 and 2, which has the capacity for up to 250 g of ethylene oxide. Both of said vessels are enclosed in a ventilated cabinet separate from the cabinet that encloses the sterilizing chamber. The outlet valve of the bulk supply vessel is closed and the outlet valve of the unit dosage vessel is opened to feed 200 g. of 100% ethylene oxide into the sterilizing chamber. To facilitate the charging of ethylene oxide to the sterilizing chamber, a vacuum is drawn on the chamber so that only the bulk supply vessel and the charging system contain ethylene oxide at above atmospheric pressure. As the ethylene oxide enters the sterilizing chamber, it impinges against a plate designed to distribute the ethylene oxide within the chamber. The ethylene oxide evaporates and is maintained in contact with the load of linens for about 30–120 minutes, depending on the particular materials being processed, which is sufficient to sterilize the material.

An important safety advantage of the use of an integral unit dosage container as described is that it ensures that a small and correct amount of sterilant is charged to the sterilizing chamber and protects against possible failure of the outlet valve of the bulk supply vessel or failure of automatic controls. In the event of such failures and the absence of a unit dosage vessel, a catastrophically dangerous excess of flammable sterilant gas could be fed to the sterilizing cabinet. Because of such risks, the charging of sterilant gas to a sterilizing chamber directly from a shipping cylinder (bulk supply vessel) normally is not permitted in hospitals. Such risk has led to the use of the small unit dose cartridges. The use of a non-disposable, separately enclosed unit dosage vessel in accordance with the invention avoids the danger of direct feeding from large containers and avoids the expense and hazards of small disposable unit dose cartridges.

Although the supply cabinet 14 containing a unit dose vessel as illustrated is highly advantageous, it is also within the scope of the invention to store conventional unit dose cartridges in the novel supply cabinet. The sturdily constructed cabinet having ventilation means and means for flooding the cartridges with waters provides a safe storage zone for ethylene oxide cartridges. Containment of the cartridges under water prevents deflagration even though a cartridge ruptures.

Although the invention has been described in detail with ethylene oxide as the sterilizing gas, it should be understood that the apparatus and process of the invention are broadly useful with other alkylene oxide sterilant gases and, in fact, with any flammable or toxic gaseous sterilant.

The invention has been described with particular reference to preferred embodiments thereof, but it will be understood that variations and modifications can be effected within the spirit and scope of the invention, and the foregoing description should be taken as illustrative and not in a limiting sense.

I claim:

1. A chemical sterilization method comprising:

storing a multi-dosage amount of a flammable chemical sterilant gas under pressure in a bulk storage container in a containment zone provided with means for flooding said zone with water, a supply cabinet enclosing said bulk storage container and said containment zone, intermittently feeding a unit dosage of said sterilant gas from said bulk container to a unit dosage container of smaller volume, intermittently feeding the contents of said unit dosage container to a chemical sterilization chamber containing material to be sterilized, and ventilating said cabinet to maintain a subatmospheric pressure within the supply cabinet.

2. The method according to claim 1 further comprising:

monitoring for a loss of ventilation; and flooding said zone to immerse said container in water upon detection of loss of ventilation.

3. A method of reducing a danger of fire or explosion of an ethylene oxide sterilant in an event of an emergency, the method comprising:

supplying the ethylene oxide sterilant from a bulk storage container to a unit dosage container;

supplying a unit dosage of the ethylene oxide sterilant from the unit dosage container to a sterilization chamber containing items to be sterilized;

detecting for leakage of ethylene oxide sterilant into a contained area adjacent the bulk storage container including:

chemically sensing whether a concentration of ethylene oxide in the contained area is above a threshold concentration; and, delivering a supply of an aqueous liquid to at least the area adjacent the bulk storage container when at least the threshold concentration of leaking ethylene oxide sterilant is detected.

4. The method of claim 3, wherein the step of delivering a supply of an aqueous liquid further comprises:

immersing the bulk storage container in the aqueous liquid.

5. The method of claim 3, further comprising:

enclosing at least the bulk storage container in a cabinet, and the step of monitoring for leakage of ethylene oxide sterilant including chemically sensing the concentration of ethylene oxide in an interior of the cabinet, the step of delivering a supply of an aqueous liquid including delivering the aqueous liquid to the interior of the cabinet.

6. The method of claim 3, wherein the aqueous liquid is water.

7. The method of claim 6, wherein the threshold concentration of leaking ethylene oxide sterilant is about 30,000 ppm.

8. A method of supplying a volatile sterilant to a sterilizer comprising:

supplying a volatile sterilant from a bulk storage container to a unit dosage container, at least the bulk storage container being enclosed in a cabinet, the cabinet including a scrubber which provides surfaces for gas-liquid contact;

supplying a unit dosage of the volatile sterilant from the unit dosage container to a sterilization chamber containing items to be sterilized;

detecting for leakage of sterilant including detecting leaks in an interior of the cabinet;

delivering a supply of an aqueous liquid to at least the interior of the cabinet when at least a preselected concentration of leaking sterilant is detected; and, passing aqueous liquid through the scrubber.

9. A method of supplying a volatile sterilant to a sterilizer comprising:

supplying a unit dosage of a volatile sterilant from a bulk storage container to a sterilization chamber containing items to be sterilized;

enclosing at least the bulk storage container within a cabinet;

ventilating the cabinet;

maintaining an interior of the cabinet at a subatmospheric pressure;

detecting for at least one of inadequate cabinet ventilation and leakage of volatile sterilant, including detecting for an increase in pressure in the interior of the cabinet; and, delivering a supply of a combustion quenching liquid to the interior of the cabinet in response to a pressure in the interior of the cabinet rising above a preselected level.

10. The method of claim 9 wherein the cabinet also encloses a unit dosage container for metering unit doses of the volatile sterilant, and wherein the step of supplying a unit dosage of the volatile sterilant from the bulk storage container to the sterilization chamber includes metering the unit dosage into the unit dosage container.

11. A method of supplying volatile sterilant to a sterilizer, the method comprising;

storing cartridges of flammable volatile sterilant in a cabinet, said cartridges configured for engagement with a sterilant supply system of a sterilizer for supplying sterilant to the sterilizer;

maintaining a subatmospheric pressure within the cabinet;

monitoring for an increase in pressure within the cabinet; and on detection of the increase in pressure, flooding the cabinet with a fluid which includes water to submerge the cartridges stored therein and prevent deflagration by ingition of the flammable volatile sterilant leaking from the cartridges.

* * * * *